United States Patent [19]

Griott

[11] Patent Number: 5,256,062
[45] Date of Patent: Oct. 26, 1993

[54] COMBINATION METALLIC CERAMIC ORTHODONTIC BRACKER

[75] Inventor: Donald E. Griott, San Marcos, Calif.

[73] Assignee: Johnson & Johnson Consumer Products, Inc., Skillman, N.J.

[21] Appl. No.: 906,602

[22] Filed: Jun. 30, 1992

[51] Int. Cl.$^5$ .............................. A61C 3/00
[52] U.S. Cl. .............................. 433/9; 433/8
[58] Field of Search ............. 433/8, 9, 10, 11, 12, 433/13, 14, 15, 16, 17

[56] References Cited

U.S. PATENT DOCUMENTS

| | | | |
|---|---|---|---|
| 3,496,637 | 2/1970 | Etengoff | 433/8 X |
| 4,545,760 | 10/1985 | Forster | 433/9 X |
| 4,565,526 | 1/1986 | Kawata et al. | 433/8 |
| 4,626,209 | 12/1986 | Tsai et al. | 433/9 |
| 4,639,218 | 1/1987 | Jones et al. | 433/8 |
| 4,889,485 | 12/1989 | Iida | 433/9 |
| 4,904,188 | 2/1990 | Baurmash | 433/9 X |
| 4,948,366 | 8/1990 | Horn et al. | 433/8 X |
| 4,952,142 | 8/1990 | Nicholson | 433/9 |
| 5,110,290 | 5/1992 | Wong | 433/9 |

Primary Examiner—John J. Wilson
Assistant Examiner—Nicholas D. Lucchesi
Attorney, Agent, or Firm—Paul A. Coletti

[57] ABSTRACT

A dental bracket is described which comprises a non-metallic bracket, typically formed from a transparent crystalline alumina. To this non-metallic bracket there is bound a stainless steel metallic foil mesh pad which is adhesively connected to the dental bracket. The foil mesh pad can thereafter be bound to the tooth using typical adhesives, and without worrying of bonding or debonding associated with ceramic or crystallic brackets. If desired, one can make the stainless steel pad aesthetically pleasing, to obtain further aesthetic benefits from this device.

8 Claims, 1 Drawing Sheet

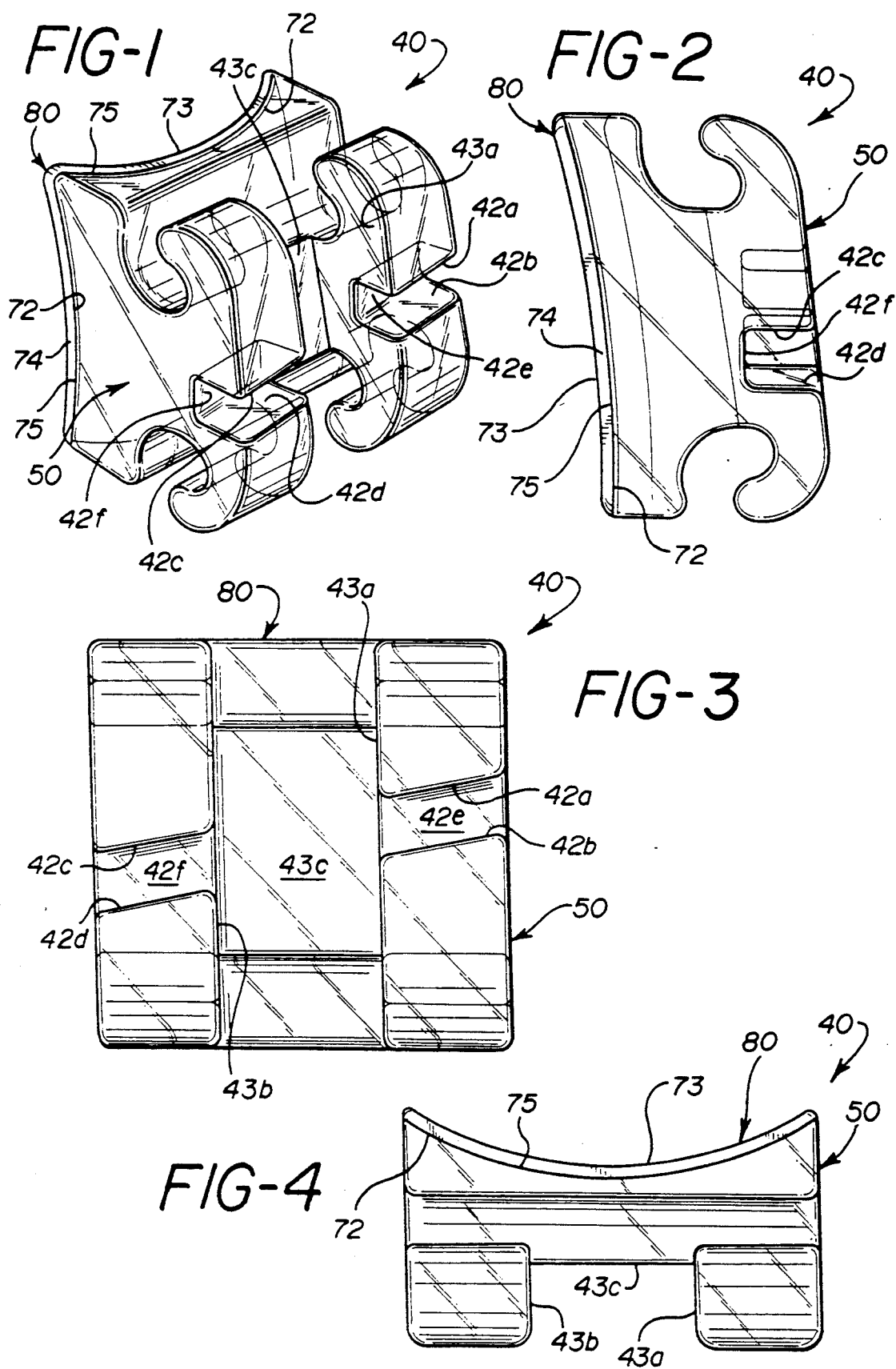

COMBINATION METALLIC CERAMIC ORTHODONTIC BRACKER

FIELD OF THE INVENTION

This invention relates generally to orthodontic brackets, and more specifically to a ceramic orthodontic bracket with a metallic base pad attached to it for ease of adhesion to, and ease of removal from the mouth.

BACKGROUND OF THE INVENTION

Orthodontic brackets are attached directly to teeth and serve to transmit corrective forces from an orthodontic archwire to the tooth to which the bracket is attached. The requirements of an orthodontic bracket are quite severe. First, it must have sufficient mechanical strength to withstand the forces to which it will be subjected. Exemplary forces are those transmitted by an archwire, by ligation, and by mastication. Second, the bracket must be chemically inert so that it will not corrode and also remain biologically compatible. Third, the bracket must be small enough to fit on the tooth.

Although there have been proposals for making orthodontic brackets from many different materials, the overwhelming majority of orthodontic brackets are still made of metal, usually stainless steel. Metal brackets meet all of these essential requirements but have one undesirable attribute —they are visible. A person undergoing orthodontic treatment has a conspicuous amount of metal in full view on the front surfaces of the teeth. And, since the treatment extends over a number of years, this appearance must be endured for a considerable period of time.

The incentive to make brackets from less unsightly materials has existed for many years. Recently, orthodontic treatment has given to an increasing number of adults, for whom the appearance of metal brackets is more than a mere annoyance. To avoid this unsightly visage, there have been proposed to make orthodontic brackets of less conspicuous materials, such as transparent or translucent plastics (such as polycarbonate), or ceramic materials which more closely resemble natural teeth. Also, it has been proposed to make these ceramic or plastic brackets with reinforcing metal inserts or liners for an archwire group. Most recently, there have been proposed orthodontic brackets comprising a crystalline alumina such as crystalline alpha-alumina. The strength and transparency properties of crystalline alumina and certain other crystalline alpha-alumina materials permit the provision of orthodontic brackets that are much more aesthetic than metal brackets but which alleviate to a large degree the strength limitations of plastic and ceramic brackets.

Nonetheless, there is still a problem with the crystalline alumina or "sapphire" orthodontic brackets. This is contained in the bonding mechanism for bonding the brackets to the teeth. That is, while the nonmetallic materials are desirable for use in providing aesthetic appearances, they are less than desirable in bonding to the teeth. This is true due both to inadequacies of the bond, and to the tendency of these nonmetallic brackets to remain bonded to the tooth even when it is desired to remove them from the mouth. This brings about a less than desirable result, from an aesthetic viewpoint when chemical debonding agents must be used to remove such stubbornly adhesive brackets.

SUMMARY OF THE INVENTION

Therefore, it is an object of the invention to provide an aesthetic bracket which bonds and debonds from the tooth with the capabilities of a metallic dental bracket.

It is another object of the invention to provide a dental bracket which is capable of being aesthetically pleasing in that it provides a natural coloring, or even a transparent surface along all its sides.

Finally, it is an object of the invention to provide a dental bracket assembly wherein the base pad of the bracket assembly is adherently bound via a naturally colored adhesive to the rear surface of the dental bracket.

These and other objects of the invention are accomplished in a dental bracket assembly comprising a nonmetallic dental bracket with a tooth facing surface. This nonmetallic bracket may be formed from any crystalline alpha alumina or ceramic or plastic. It is specifically intended that the dental bracket be transparent for aesthetic purposes. Adhesively bound to the bracket is a metallic pad. Preferably, the metallic pad is formed from a foil mesh. The metallic pad is generally made of stainless steel. This foil mesh is capable of being bound to the surface of the tooth via typical adhesives used with stainless steel brackets. Moreover, the metallic pad is bound to the nonmetallic bracket using certain other adhesives. Furthermore, it is possible to glaze or bake the adhesive to the nonmetallic surface of the bracket so that aesthetics are improved.

Results of using the foregoing bracket allow orthodontists to provide improved aesthetic brackets to the patient, yet furthermore allow for the earlier referenced desirable adhesion and removal of metallic base pads.

These aspects of the invention will be better understood from the attached Brief Description of the Drawings taken in conjunction with the following Detailed Description of the Invention.

BRIEF DESCRIPTION OF THE DRAWINGS

FIG. 1 is a perspective view of an orthodontic bracket formed from a transparent material, and with a metallic pad attached to it;

FIG. 2 is a side view of the bracket of FIG. 1;

FIG. 3 is front view of the bracket of FIG. 1; and

FIG. 4 is top view of the bracket of FIG. 1.

DETAILED DESCRIPTION OF THE DRAWINGS

The device of this invention is a dental bracket assembly 40 containing an orthodontic bracket 50 comprising a load bearing member made from crystalline alumina materials, preferably crystalline alpha-alumina. As used herein, "crystalline alumina" in intended to include both monocrystalline aluminas and polycrystalline aluminas. In a preferred aspect of the invention, the orthodontic bracket is entirely crystalline alpha-alumina. In other aspects of the invention, the orthodontic bracket is formed from a ceramic or transparent plastic. What is most desired is that the orthodontic bracket 50 be virtually transparent and yet be able to maintain or bear loads. One such orthodontic bracket is described in U.S. Pat. No. 4,639,218 to Jones et al. and assigned to Johnson & Johnson Dental Products Company, an affiliate company of the Assignee of this patent application.

FIGS. 1-4 are various views of an orthodontic bracket assembly 40 made from a ceramic or crystalline alumina bracket 50 and having attached to it a stainless steel pad 80. As seen therein, the dental bracket 50 has an archwire groove defined by sidewalls 42a, 42b, 42c, 42d, 42e, 42f, and a "saddle" defined by walls 43a, 43b, 43c of a double wing or twin bracket. Most importantly, the bracket 50 has a tooth facing surface 72. This surface is generally concave and is formed by applying a diamond grinding wheel to the surface 72 of the crystalline alumina bracket 50.

As can be seen in the various Figures, there is also described herein a base pad 80. This base pad has a front surface 75, a rear surface 73 and a pair of side surfaces 74. The base pad 80 is formed so that the first or front surface 75 is capable of being identically mated with the rear or tooth facing surface 72 of the dental bracket 50.

Generally, as described in this invention the pad 80 is formed from the stainless steel. Preferably, the stainless steel may be formed as a foil mesh. It has been found that the foil mesh front surface 75 when bound with a adhesive glue such as Loctite 447 TM Glue provided by Loctite Corporation, it is able to be adherently bound to the ceramic bracket 50 at surface 72.

When the base pad 80 is desired to be bound to the tooth the user applies typical stainless steel dental bracket adhesives to the surface 73 and applies that surface to the tooth. Thus, the problems associated with adhesion of dental brackets are avoided. The dentist is able to adequately bond and debond the stainless steel surface 73 from the tooth surface, using known techniques.

An alternate preferred embodiment of the pad 80 can also be realized herein. The surface 75 of pad 80 can be coated with porcelain. Therefore, the porcelain surface 75 is exposed through the mouth, and to surface 72 of the dental bracket 50. It has been found that porcelain baked on the mesh pad 80 is still able to adequately hold a glue such as the Loctite 447 TM glue, so that the dental bracket is able to be bound thereto.

Another method of binding the ceramic bracket 50 to the base pad 80 are techniques such as brazing. There, the brazing material itself may be of a different coloration than the stainless steel pad 80 so that there is not so much steel visually observable on the pad 80 when attached to the tooth. Finally, it has been found that Loctite 447 TM glue with white dye added are able to provide a natural coloration to the stainless steel pad. Thus, as seen through the dental bracket 50, the user observes only the tooth or white colored surface of the pad 80, and therefore there is much more aesthetic acceptance of the bracket of this invention attached to the tooth.

Therefore, it has been observed that the stainless steel pad 80 in combination with the aesthetic dental bracket 50 form a unique combination which provide aesthetics, strength, and ease of bonding and debonding. Therefore, it is desired to obtain a patent for such combination as described by the appended claims and their equivalents.

I claim:

1. A dental bracket assembly comprising:
   a non-metallic dental bracket, said bracket having a tooth facing surface; and
   a metallic pad adherently connected to said tooth facing surface, said metallic pad having a first surface adapted to conform to said tooth facing surface, and a second surface adapted to be placed on a tooth wherein said first surface has attached to it a coating of porcelain for attachment to said tooth facing surface.

2. The bracket assembly of claim wherein said metallic pad is formed from stainless steel.

3. The bracket assembly of claim 1 wherein said non-metallic bracket is formed from crystalline alumina.

4. The bracket assembly of claim 1 further comprising said metallic pad formed as a foil mesh.

5. The bracket assembly of claim 1 wherein said pad is brazed to said non-metallic bracket.

6. A dental bracket assembly comprising:
   a dental bracket formed from a ceramic material, said bracket having a tooth facing surface; and
   a stainless steel pad having a first surface adherently attached to said tooth facing surface, and a second surface adapted to be attached to a tooth and wherein said first surface has attached to it a coating of porcelain for attachment to said tooth facing surface.

7. A dental bracket assembly comprising:
   a transparent dental bracket formed from a crystalline alumina and containing a tooth facing rear surface; and
   a foil mesh metallic pad having a first surface adherently attached to said tooth facing surface, and a second surface adapted to be attached to a tooth;
   wherein said first surface is attached to said tooth facing surface such that said first surface is visible through said dental bracket and wherein said first surface has attached to it a coating of porcelain for attachment to said tooth facing surface.

8. The bracket assembly of claim 7 wherein said metallic pad is formed from stainless steel.

* * * * *

UNITED STATES PATENT AND TRADEMARK OFFICE
CERTIFICATE OF CORRECTION

PATENT NO. : 5,256,062
DATED : October 26, 1993
INVENTOR(S) : Donald E. Griott

It is certified that error appears in the above-indentified patent and that said Letters Patent is hereby corrected as shown below:

On the title page: Item [21] Appl. No: "906,602" should be -- 906,601 --.

Item [54] and Column 1, line 2, "BRACKER" should read --BRACKET--.

Signed and Sealed this

Eighth Day of August, 1995

Attest:

BRUCE LEHMAN

Attesting Officer     Commissioner of Patents and Trademarks